United States Patent [19]

Brechbühler et al.

[11] 4,000,272
[45] Dec. 28, 1976

[54] CONTROL OF CERTAIN INSECTS OF THE ORDER DIPTERA WITH DIAMINO-AZIDO-S-TRIAZINES

[75] Inventors: Hans Ulrich Brechbühler, Basel; René Bosshard, Birsfelden; Dagmar Berrer, Riehen, all of Switzerland

[73] Assignee: Ciba-Geigy Corporation, Ardsley, N.Y.

[22] Filed: Nov. 3, 1975

[21] Appl. No.: 628,178

Related U.S. Application Data

[63] Continuation-in-part of Ser. No. 577,242, May 13, 1975, abandoned, which is a continuation of Ser. No. 390,630, Aug. 22, 1973, abandoned.

[30] Foreign Application Priority Data

Aug. 25, 1972 Switzerland .................. 12659/72
July 25, 1973 Switzerland .................. 10880/73

[52] U.S. Cl. ............................................. 424/226
[51] Int. Cl.² ........................................ A01N 9/22
[58] Field of Search ................................ 424/226

[56] References Cited

UNITED STATES PATENTS

| | | | |
|---|---|---|---|
| 3,326,913 | 6/1967 | Schulz et al. | 260/249.6 |
| 3,328,400 | 6/1967 | Schulz et al. | 260/249.6 |
| 3,415,827 | 12/1968 | Nikles et al. | 260/249.6 |

FOREIGN PATENTS OR APPLICATIONS

| | | |
|---|---|---|
| 1,396,616 | 3/1965 | France |
| 1,458,939 | 10/1966 | France |

OTHER PUBLICATIONS

Borkovec, Insect Chemosterilants, 1966, pp. 61–63.
Slama, Annual Review of Biochemistry, vol. 40, pp. 1079, 1096 & 1097, (1971).

*Primary Examiner*—Jerome D. Goldberg
*Assistant Examiner*—Allen J. Robinson
*Attorney, Agent, or Firm*—Frederick H. Rabin

[57] ABSTRACT

Insects of the families *Musca, Aedes* and *Lucilia* are combatted by application thereto of s-triazine derivatives of the formula

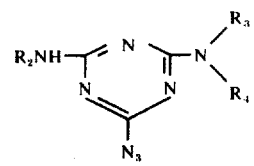

wherein $R_2$ is hydrogen, $C_1$–$C_3$ alkyl, allyl or propargyl; $R_3$ is hydrogen, methyl or ethyl; and $R_4$ is hydrogen, $C_1$–$C_3$ alkyl or propargyl.

11 Claims, No Drawings

CONTROL OF CERTAIN INSECTS OF THE ORDER DIPTERA WITH DIAMINO-AZIDO-S-TRIAZINES

CROSS-REFERENCE TO RELATED APPLICATIONS

This is a continuation-in-part of application Ser. No. 577,242 filed May 13, 1975, which is a continuation of application Ser. No. 390,630 filed Aug. 22, 1973, both now abandoned.

DETAILED DISCLOSURE

The present invention relates to a method of combatting insects, which comprises the use of s-triazine derivatives of the formula

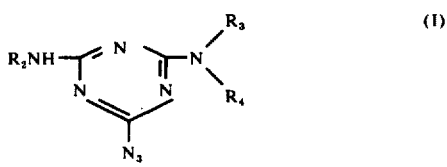

wherein $R_2$ is hydrogen, $C_1$–$C_3$ alkyl, allyl or propargyl; $R_3$ is hydrogen, methyl or ethyl; and $R_4$ is hydrogen, $C_1$–$C_3$ alkyl or propargyl. More particularly, it relates to control of insects of the families *Musca*, *Aedes* and *Lucilia* by applying these compounds to said insects when they are in the larval or pupal stages.

To be particularly highlighted on account of their action are compounds of the formula I, wherein $R_2$ represents hydrogen, methyl, ethyl, isopropyl, allyl or propargyl, and $R_4$ represents hydrogen, methyl, ethyl, isopropyl or propargyl. More particularly preferred are compounds wherein $R_2$ is hydrogen, methyl or ethyl and $R_4$ is hydrogen, methyl, ethyl or isopropyl.

Examples of compounds of the formula I include:

| No. | Name | Melting point |
|---|---|---|
| 1 | 4-azido-2,6-bis(ethylamino)-s-triazine | 102–103° C |
| 2 | 4-azido-2-ethylamino-6-isopropylamino-s-triazine | 77–79° C |
| 3 | 4-azido-2,6-bis(isopropylamino)-s-triazine | 96–97° C |
| 4 | 4-azido-2-ethylamino-6-dimethylamino-s-triazine | 163–164° C |
| 5 | 4-azido-2-amino-6-ethylamino-s-triazine | 139–144° C |
| 6 | 4-azido-2-amino-6-methylamino-s-triazine | 202–204° C |
| 7 | 4-azido-2-amino-6-isopropylamino-s-triazine | 71–72° C |
| 8 | 4-azido-2,6-bis(methylamino)-s-triazine | |
| 9 | 4-azido-2-methylamino-6-ethylamino-s-triazine | 114° C |
| 10 | 4-azido-2,6-bis(dimethylamino)-s-triazine | 103–105° C |
| 11 | 4-azido-2-methylamino-6-dimethylamino-s-triazine | |
| 12 | 4-azido-2-methylamino-6-isopropylamino-s-triazine | 101–102° C |
| 13 | 4-azido-2-amino-6-allylamino-s-triazine | 130–131° C |
| 14 | 4-azido-2-amino-6-diethylamino-s-triazine | 159–160° C |
| 15 | 4-azido-2-ethylamino-6-propargylamino-s-triazine | 117–118° C |
| 16 | 4-azido-2,6-bis(propargylamino)-s-triazine | 153° C |
| 17 | 4-azido-2-amino-6-propargylamino-2-triazine | |
| 18 | 4-azido-2-amino-6-dimethylamino-s-triazine | |

The majority of the compounds encompassed by the formula I are known or can be manufactured by methods analogous to known ones, for example a. by reaction of a chloro-bis(amino)-s-triazine of the formula

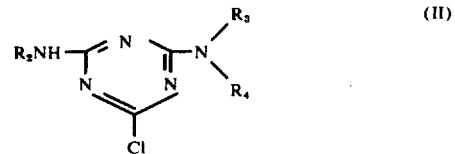

wherein $R_2$, $R_3$ and $R_4$ have the meanings given for the formula I, with an alkali metal azide in the presence of a basic substance, or b. by reaction of the compound of the formula II with hydrazine and reaction of the intermediate product of the formula

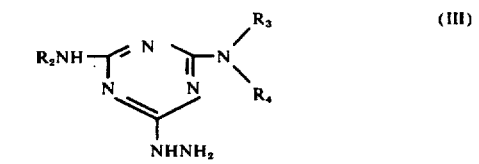

wherein $R_2$, $R_3$ and $R_4$ have the meanings given for the formula I, with nitrous acid or an alkali metal nitrite, or c. by reaction of a compound of the formula $$\begin{bmatrix} R_2NH-\overset{N}{\underset{N}{\diagup}}\overset{\diagup R_3}{\underset{\diagdown R_4}{N}} \\ CH_3-\overset{|}{N}-CH_3 \\ CH_3 \end{bmatrix}^+ Y^- \quad (IV)$$

wherein $R_2$, $R_3$ and $R_4$ have the meanings given for the formula I and Y represents an inorganic or organic acid radical, especially chlorine, bromine, or iodine, with an alkali metal azide.

Suitable basic substances are in particular tertiary amines, e.g., trialkylamines, also hydroxides, oxides, and carbonates of alkali metals and alkaline earth methals. Water is preferably used as solvent or diluent for the reactions, but it is also possible to use organic solvents which are miscible with water, e.g. ketones, ethers and ethereal compounds, nitriles, N,N-disubstituted amides, sulphoxides etc., as well as solvents which are immiscible with water, for example aliphatic and aromatic hydrocarbons and hydrogen halides.

Similar or analogous compounds are in part described as total herbicides and selective herbicides in U.S. Pat. No. 3,326,913. Similar compounds are also described as herbicides in U.S. Pat. No. 3,415,827. Attention is drawn to their possible insecticidal action.

In comparison with these active substances, the compounds of the formula I exhibit a distinct superiority in the fly test. The compounds of the formula I are suitable for combatting insects, particularly members of the families *Musca*, *Aedes* and *Lucilia*. In contradistinction to the classical insecticides, which in the form of contact or ingest poisons kill or paralyze the insects within a few hours, the active substances of the formula I influence primarily the larval development. The activity consists in killing the egg larvae or in preventing adult insects from hatching from pupae. This mode of action is not comparable with classical insecticides, chemosterilants, or juvenile hormones.

The compounds of the formula I may be used as pure active substance or together with suitable carriers and/or additives. Suitable carriers and additives can be solid or liquid and correspond to the substances conventionally used in formulation technique such, for example, as solvents and/or dispersants.

The agents according to the invention are manufactured in known manner by intimately mixing and/or grinding active compounds of the formula I with suitable carriers, optionally with the addition of dispersants or solvents which are inert towards the active compounds. The active compounds may take, and may be used in, the following forms:

Solid forms:
  Dusts, baits, granules, (coated granules, impregnated granules and homogeneous granules).
Liquid forms:
  a. active substances which are dispersible in water: wettable powders, pasts, emulsions;
  b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active compounds and in the process of which the granulation is carried out during the gel formation. It is more advantageous to impregnate finished, porous polymer granules (urea/formaldehyde, polyacrylonitrile, polyester or others) which have a specific surface area and a favourable predeterminable absorption/desorption ratio, with the active ingredients for example in the form of their solutions (in a low boiling solvent) and to remove the solvent. Polymer granules of this kind in the form of microgranules having a bulk density of 300 g/liter to 600 g/liter can also be manufactured with the aid of atomisers.

It is also possible to obtain granules by compacting the carrier with the active ingredient and subsequently comminuting the product.

To these mixtures can also be added additives which stablise the active ingredient and/or non-ionic, anionic and cationic surface active substances, which, for example, ensure a better wettability (wetting agents) and dispersibility (dispersing agents).

The water-dispersible concentrates of the active substance, i.e., wettable powders, pastes and emulsifiable concentrates, are agents which can be diluted with water to any concentration desired. They consists of active compound, carrier, optionally additives which stabilise the active substance, surface-active substance and anti-foam agents and, optionally, solvents.

Wettable powders and pastes are obtained by mixing and grinding the active ingredients with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl, dilauryl ammonium chloride and fatty acid alkali and alkaline earth metal salts.

Suitable anti-foam agents are silicones.

The active substances are mixed, ground, sieved and strained with the additives cited hereinabove, in such a manner that, the size of the solid particles does not exceed 0.02 to $0.04\mu$ in wettable powders, and $0.03\mu$ in pastes. To produce emulsifiable concentrates and pastes, dispersing agents such as those cited above, organic solvents, and water are used. Examples of suitable solvents are: alcohols, dimethyl sulphoxide, and mineral oil fractions which boil between 120° and 350° C. The solvents must be practically odourless and inert to the active substances.

Furthermore, the agents according to the invention can be applied in the form of solutions. For this purpose the active compounds, or several active compounds of the general formula I, are dissolved in suitable organic solvents, mixtures of solvents or in water. Aliphatic and aromatic hydrocarbons, chlorinated derivatives thereof, alkyl naphthalene and mineral oils, singly or in admixture with each other, can be used as organic solvents.

The active compounds of the formula I can, for example, be formulated as follows:

Dusts:
The following substances are used to manufacture a) a 0.5% and b) a 2% dust:
  a) 5 parts of active compound,
     95 parts of talcum
  b) 2 parts of active compound
     1 part of highly disperse silicic acid
     97 parts of talcum.

The active compounds mixed with the carriers and ground.

Baits
  5 parts of active compound mixed with
  95 parts of carbonate of lime and ground to an average -continued particle size of 80μ.

Granules:
- 5 parts of active substance are dissolved in a solvent, e.g. methylene chloride, and mixed with
- 2 parts of polyethylene glycol ("Carbowax").
- 91.5 parts of calcium carbonate are impregnated with the mixture and
- 1.5 parts of precipitated silicic acid are admixed.

The solvent is subsequently evaporated.

Wettable Powder:
- 50 parts of active substance are mixed with
- 5 parts of a dispersing agent, e.g. sodium lignin sulphonate,
- 5 parts of a wetting agent, e.g. dibutylnaphthalene-sulphonic acid
- 10 parts of silicic acid and
- 30 parts of China clay and the mixture is finely ground.

Emulsifiable Concentrate:
- 20 parts of active substance are mixed with
- 20 parts of emulsifier, e.g. a mixture of alkylaryl-polyglycol ether with alkylarylsulphonates, and
- 60 parts of solvent until the solution is completely homogeneous. By diluting this concentrate with water it is possible to obtain an emulsion of any desired concentration.

Premix (animal feed additive):
- 0.25 part of active compound and
- 4.75 parts of secondary calcium phosphate, or China clay, aerosil or carbonate of lime are homogenously mixed with 95 parts of an animal feed, e.g., rabbit food.

Spray:
The following constituents are used to manufacture a 2% spray:
- 2 parts of active compound
- 98 parts of kerosene.

Other biologically active substances or agents can be admixed with the agents described hereinabove. Thus in addition to the cited compounds of the general formula I, the new agents can contain, for example, insecticides to broaden the spectrum of activity.

The agents, or the active compounds contained therein, exert their inhibitory action therefore chiefly on the development of larvae or pupae of insects in the families *Musca*, *Aedes* and *Lucilia*, of the order *Diptera*.

EXAMPLE 1

| | Example 1 |
|---|---|
| Test substances: | Active compounds of the formula I formulated as solutions in acetone. |
| Test subject: | Musca Domestica (housefly) |
| Concentration: | 0.05% of active compound |
| Test method: | 50 g of CSMA maggot substrate are weighed at a time in beakers. 2.5 ml of a 1% solution of acetone of each active substance are pipetted twice on 50 g of substrate. The treated substrate is thoroughly mixed and the solvent then evaporated. Then 2 × 25 one-day old maggots of Musca Domestica are applied to active substance. After 5 days the pupae are flushed out and the hatching rate and morphological affects (i.e. abnormal metamorphosis) are determined after 10 days |

The results are as follows:

| Compounds | number of living larvae | number of abnormal pupae | number of normal adult flies |
|---|---|---|---|
| 2 | 0 | 42 | 0 |
| 1 | 0 | 49 | 0 |
| 5 | 0 | 5 | 0 |
| 7 | 0 | 18 | 0 |
| 14 | 4 | 1 | 0 |
| 15 | 0 | 8 | 0 |
| 9 | 0 | 9 | 0 |
| 18 | 0 | 43 | 0 |
| 17 | 0 | 23 | 0 |
| untreated control | — | — | 50 |

EXAMPLE 2

| | Example 2 |
|---|---|
| Test substances: | Active compounds of the formula I formulated as solutions in acetone. |
| Test subject: | Aedes aegypti (mosquitoes) |
| Concentration: | 5 ppm of active compound |
| Test method: | A quantity of a 0.1% acetonic solution of each active substance is pipetted onto the surface of 150 ml of water contained in a beaker. After evaporation of the acetone 40 days old Aedes larvae are introduced into each beaker, a beaker being employed at each concentration. Crumbled dog-biscuits are added and the beaker covered with a copper ganze lid. After 1, 2 and 5 days mortality and morphological effects (i.e. abnormal metamorphosis) are determined. |

The results are as follows:

| Compounds | percentage of mortality of the larvae | number of abnormal larvae | number of pupae |
|---|---|---|---|
| 2 | 65 | 3 | 10 (abnormal) |
| 1 | 100 | 0 | 0 |
| 5 | 100 | 0 | 0 |
| 14 | 100 | 0 | 0 |
| untreated control | 0 | 0 | 40 normal pupae |

EXAMPLE 3

| | Example 3 |
|---|---|
| Test substances: | Active compounds of the formula I formulated as solutions in water |
| Test subject: | Lucilia sericata (blowfly) |
| Concentration: | 0.025% of active ingredient |
| Test method: | 1 ml of an aqueous solution containing 0.25% of the active ingredient are mixed with 9 ml of a special blowfly-larvae rearing medium (Yolk powder/B.H.I./Agar) at 50° C to give a mixture containing 0.025% (250 ppm) active ingredient. Approximately 30 freshly hatched blow-fly larvae are then added. After 96 hours the insecticidal effect is determined. |
| Results: | All of the compounds tested - Nos. 1, 2, 5, 7, 14, 15, 17 and 18 - showed 100% mortality. |

We claim:

1. A method of combatting insects of the family *Musca*, *Aedes* and *Lucilia* which comprises applying to said insects in their larval or pupal stage, in sufficient amount to inhibit metamorphosis, a compound of the formula

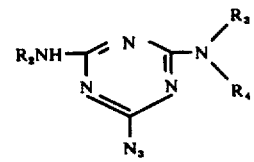

in which $R_2$ is hydrogen, $C_1$–$C_3$ alkyl, allyl or propargyl, $R_3$ is hydrogen, methyl or ethyl, and $R_4$ is hydrogen, methyl, $C_1$–$C_3$ alkyl or propargyl.

2. The method according to claim 1 in which $R_2$ is hydrogen, methyl or ethyl, and $R_4$ is hydrogen, methyl, ethyl or isopropyl.

3. The method of claim 2 in which the compound is 4-azido-2,6-bis(ethylamino)-s-triazine.

4. The method of claim 2 in which the compound is 4-azido-2-ethylamino-6-isopropylamino-s-triazine.

5. The method of claim 2 in which the compound is 4-azido-2-amino-6-ethylamino-s-triazine.

6. The method of claim 2 in which the compound is 4-azido-2-amino-6-isopropylamino-s-triazine.

7. The method of claim 2 in which the compound is 4-azido-2-methylamino-6-ethylamino-s-triazine.

8. The method of claim 2 in which the compound is 4-azido-2-amino-6-diethylamino-s-triazine.

9. The method of claim 2 in which the compound is 4-azido-2-amino-6-dimethylamino-s-triazine.

10. The method of claim 1 in which the compound is 4-azido-2-ethylamino-6-propargylamino-s-triazine.

11. The method of claim 1 in which the compound is 4-azido-2-amino-6-propargylamino-s-triazine.

* * * * *